United States Patent [19]

Tamabuchi

[11] Patent Number: 4,818,521

[45] Date of Patent: Apr. 4, 1989

[54] EMULSION COSMETIC STABLY CONTAINING VITAMIN C

[75] Inventor: Hiroshi Tamabuchi, Takatsuki, Japan

[73] Assignee: Sunstar Kabushiki Kaisha, Osaka, Japan

[21] Appl. No.: 933,867

[22] Filed: Nov. 24, 1986

Related U.S. Application Data

[63] Continuation of Ser. No. 724,570, Apr. 18, 1985, abandoned.

[51] Int. Cl.$^4$ .................. A61K 7/48; A61K 7/135
[52] U.S. Cl. .................................. 424/62; 514/474; 514/887; 514/938; 514/972
[58] Field of Search ............. 514/474, 938, 887, 972; 424/62

[56] References Cited

U.S. PATENT DOCUMENTS

| | | | |
|---|---|---|---|
| 2,376,884 | 5/1945 | Schwenk et al. | 424/59 |
| 2,491,452 | 4/1949 | Kern et al. | 514/474 |
| 2,709,149 | 5/1955 | Dunmire | 514/474 |
| 3,781,423 | 12/1973 | Aoka et al. | 514/474 |
| 3,873,713 | 3/1975 | Haas et al. | 514/474 |
| 4,102,806 | 7/1978 | Kondo et al. | 514/474 |

FOREIGN PATENT DOCUMENTS

| | | | |
|---|---|---|---|
| 2383663 | 11/1978 | France | 424/62 |
| 4515391 | 5/1970 | Japan | 424/62 |
| 0120612 | 9/1981 | Japan | 424/62 |
| 0161314 | 12/1981 | Japan | 424/62 |
| 343691 | 12/1970 | U.S.S.R. | 424/62 |
| 2093346 | 9/1982 | United Kingdom | 424/62 |

OTHER PUBLICATIONS

Abstract of Japanese Patent No. 7015391, Matsumoto.

Primary Examiner—Dale R. Ore
Attorney, Agent, or Firm—Wegner & Bretschneider

[57] ABSTRACT

An emulsion cosmetic stably containing vitamin C which comprises a mixture of L-ascorbic acid or a fatty acid ester thereof and an oil, and conventional ingredients for the emulsion cosmetic.

5 Claims, No Drawings

EMULSION COSMETIC STABLY CONTAINING VITAMIN C

This application is a continuation of Ser. No. 724,570, filed Apr. 18, 1985 now abandoned.

FIELD OF THE INVENTION

The present invention relates to an emulsion cosmetic in which vitamin C is stably formulated.

BACKGROUND OF THE INVENTION

Vitamin C (L-ascorbic acid) is used as an active ingredient for various kinds of cosmetics in view of its nutritive enriching effect, fair skin producing effect and the like. However, vitamin C itself is a very unstable substance. Accordingly, in general, it is formulated in a cosmetic as a vitamin C derivative having improved stability such as L-ascorbic acid fatty acid ester, or it is formulated as a so-called two-pack type cosmetic wherein vitamin C powder and other ingredients are separately packed in different containers and they are mixed just prior to use the cosmetic.

However, the vitamin C derivative does not always have enough stability. Particularly, in an emulsion cosmetic such as a cream or a milky lotion, it tends to relatively quickly lose its vitamin C effect. In case of a two-pack type cosmetic, indeed, the stability of vitamin C is improved, but it is not satisfactory because it requires extra labor and expense for packing vitamin C and such a trouble as mixing the ingredients prior to use.

Under these circumstances, the present inventor has intensively studied to obtain a novel emulsion cosmetic in which vitamin C is stably formulated. As the result, it has been found that an emulsion cosmetic in which vitamin C is very stably formulated is obtained by previously treating vitamin C or a derivative thereof with an oil and then formulating it into the cosmetic.

OBJECTS AND SUMMARY OF THE INVENTION

The main object of the present invention is to provide an emulsion cosmetic stably containing vitamin C.

This object as well as other objects and advantages of the present invention will become apparent to those skilled in the art from the following description.

According to the present invention, there is provided an emulsion cosmetic stably containing vitamin C which comprises a mixture of L-ascorbic acid or a fatty acid ester thereof and an oil, and conventional ingredients for the emulsion cosmetic. Particularly, although most of conventional emulsion cosmetics containing vitamin C are weakly basic and emulsified with soaps or soaps and nonionic surface active agents, in the present invention, it is preferable to formulate vitamin C in an oil in water type emulsion (hereinafter referred to as O/W type emulsion) which is emulsified with a nonionic surface active agent. Further, it is preferable that the emulsion is weakly acidic. According to the present invention, vitamin C can be very stably formulated in an emulsion cosmetic without employing a two-pack form and a cosmetic having excellent nutritive enriching effect and fair skin producing effect of vitamin C can be obtained.

DETAILED EXPLANATION OF THE INVENTION

The following experiments illustrate the effect of the treatment of vitamin C with an oil as well as the natures of emulsions, to which vitamin C is formulated, on stability of vitamin C.

(1) Preparation of samples (a) Preparation of emulsion bases

Emulsions were prepared by using a conventional method according to the following formulations.

(i) Formulation of Emulsion Base I (weakly basic O/W type emulsion (pH 8.3) emulsified with a soap and a nonionic surface active agent)

| Ingredients | wt % |
|---|---|
| White bees wax | 2.5 |
| Cetanol | 2.0 |
| Stearic acid | 2.5 |
| Glyceryl monostearate (self emulsifiable type with soap) | 2.5 |
| Polyoxyethylene sorbitan monostearate (20 E.O.) | 1.5 |
| Liquid paraffin | 22.0 |
| Isopropyl myristate | 7.0 |
| Polyethylene glycol 400 | 5.0 |
| Triethanolamine | 1.0 |
| Butyl paraben | 0.1 |
| Methyl paraben | 0.1 |
| Water | remainder |

(ii) Formulation of Emulsion Base II (weakly acidic O/W type emulsion (pH 5.0) emulsified with a nonionic surface active agent)

| Ingredients | wt % |
|---|---|
| White bees wax | 2.5 |
| Stearic acid | 3.0 |
| Glyceryl monostearate (self emulsifiable type with nonionic agent) | 2.5 |
| Lanoline | 1.5 |
| Sorbitan sesquiolate | 1.5 |
| Liquid paraffin | 22.0 |
| Isopropyl palmitate | 7.0 |
| Polyethylene glycol 400 | 5.0 |
| Butyl paraben | 0.1 |
| Methyl paraben | 0.1 |
| Water | remainder |

(b) Untreated vitamin C ester L-ascorbic acid dipalmitate (c) Oil-treated vitamin C ester The oil-treated vitamin C was prepared by mixing L-ascorbic acid dipalmitate and a silicone oil (dimethyl polysiloxane-100CS) in the weight ratio of 1:1 and then kneading the mixture with a roller mill or a kneader. According to the same procedure, free L-ascorbic acid was also treated.

(d) Preparation of cream samples

To each base was added untreated vitamin C ester or the oil-treated vitamin C ester in an amount of 1% based on the total weight of the base at 70° C. and the resulting mixture was cooled with stirring to about 30° C. to obtain a cream.

(2) Test method

Each cream thus obtained was allowed to stand at −5° C., room temperature and 40° C., respectively, and the amount of L-ascorbic acid dipalmitate or L-ascorbic acid in the cream was determined at regular time intervals by using a high performance liquid chromatography [the sample (2 g) was dissolved in chloroform-ethanol-water (1:2:1) to bring the total volume to 100 ml. 20 Microliters of the resulting solution was used. Column: LC-3 type Nucreosil C-18 (SHIMAZU SEISAKUSHO K.K.); mobile phase: methanol-water (93:7), 0.01M sodium biphosphate; flow rate: 1.2 ml/min; detection wave length: 254 nm] and calculated the remaining ratio (%) thereof.

(3) Results

The results are shown in Table 1.

TABLE 1

| No. | Sample Cream | Temperature | Remaining ratio (%) Days | | | |
|-----|--------------|-------------|---|---|---|---|
| | | | 0 | 30 | 60 | 90 |
| 1 | Base I, untreated vitamin C ester | Room temp. | 76 | 37 | 20 | 6 |
| | | 40° C. | 76 | 12 | 0 | 0 |
| 2 | Base I, oil-treated vitamin C ester | Room temp. | 98 | 90 | 85 | 82 |
| | | 40° C. | 98 | 75 | 66 | 60 |
| 3 | Base II, untreated vitamin C ester | Room temp. | 80 | 50 | 36 | 20 |
| | | 40° C. | 80 | 30 | 10 | 0 |
| 4 | Base II, oil-treated vitamin C ester | Room temp. | 101 | 98 | 98 | 96 |
| | | 40° C. | 101 | 95 | 93 | 92 |
| 5 | Base II, oil-treated free vitamin C | Room temp. | 97 | 95 | 92 | 90 |
| | | 40° C. | 97 | 88 | 81 | 72 |

The same procedure of the above test No. 4 was repeated except that various kinds of oils were used for preparation of the oil-treated vitamin C ester. The results are shown in Table 2.

TABLE 2

| No. | Oils | Temperature | Remaining ratio (%) Days | | | |
|-----|------|-------------|---|---|---|---|
| | | | 0 | 30 | 60 | 90 |
| 6 | Silicon oil (Methylphenyl polysiloxane) | Room temp. | 106 | 104 | 104 | 102 |
| | | 40° C. | 106 | 101 | 98 | 95 |
| 7 | Liquid paraffin | Room temp. | 102 | 100 | 98 | 98 |
| | | 40° C. | 102 | 97 | 96 | 94 |
| 8 | Olive Oil | Room temp. | 99 | 99 | 96 | 97 |
| | | 40° C. | 99 | 95 | 96 | 90 |
| 9 | Isopropyl myristate | Room temp. | 104 | 100 | 97 | 90 |
| | | 40° C. | 104 | 86 | 84 | 81 |

As shown in Table 1, untreated vitamin C ester is not so stable in both a weakly basic O/W type emulsion emulsified with a soap and a nonionic surface active agent (Base I) and a weakly acidic O/W type emulsion emulsified with a nonionic surface active agent (Base II). However, when using the oil-treated vitamin C, stability is improved. Particularly, when the oil-treated vitamin C or the ester thereof is formulated in Base II, stability thereof is remarkably improved. Further, as shown in Table 2, the oil used for the treatment of vitamin C is not limited a specific kind of oils, but a nonpolar oil is preferred.

Thus, the emulsion cosmetic of the present invention is prepared by homogeneously dispersing and mixing a mixture of L-ascorbic acid or a fatty acid ester thereof and an oil in an emulsion, preferably, in an O/W type emulsion emulsified with a nonionic surface active agent, more preferably, in a weakly acidic O/W type emulsion.

The L-ascorbic acid used may be in the form of either a free acid or a fatty acid ester. Examples of the fatty acid ester include mono-, di- or triesters of fatty acids having 10 or more carbon atoms such as monopalmitate, dipalmitate, monostearate and distearate thereof.

As mentioned above, the oil used for preparation of the above mixture is not limited to a specific one. Although oils having relatively higher polarity such as isopropyl myristate may show a good effect, in general, high hydrophobic oils, for example, various silicone oils, hydrocarbons such as liquid paraffin and squalane, animal and vegetable oils such as castor oil and olive oil, and the like are especially preferred.

The amount of the above oil used may be different depending upon its viscosity, desired amount of vitamin C to be formulated in the cosmetic. However, preferably, the amount is within a range of a weight ratio thereof to L-ascorbic acid or a fatty acid ester thereof being about 1:0.5 to 4. The mixture can be prepared by mixing L-ascorbic acid or a fatty acid ester thereof with an oil and thoroughly kneading the resulting mixture with, for example, a roller mill or a kneader at room temperature.

The emulsion itself may be a conventional one prepared by using conventional ingredients according to a standard method. For example, there can be used an emulsion emulsified with a soap which comprises a higher fatty acid and a base such as an organic amine or borax. Preferably, an emulsion emulsified with one or more kinds of nonionic surface active agents such as sorbitan higher fatty acid esters, polyoxyethylene sorbitan higher fatty acid esters, glycerol higher fatty acid esters, polyoxyethylene higher alcohol ethers according to a standard method can be used.

Other ingredients are not limited to specific materials and all conventional ingredients for an emulsion cosmetic can be used.

The cosmetic of the present invention can be prepared by, after preparation of the emulsion, adding a mixture of L-ascorbic acid or a fatty acid ester thereof to the emulsion at about 50° to 70° C. with stirring, dispersing the mixture, cooling the resulting latter mixture with stirring and optionally adding a flavor and the like. The cosmetic of the present invention can be prepared in a conventional form such as a cream or a milky lotion. The amount of L-ascorbic acid or a fatty acid ester thereof to be added to the cosmetic of the present invention can be appropriately chosen according to a desired effect or a particular form of the cosmetic. In general, however, it is preferable to add L-ascorbic acid or a fatty acid ester thereof in an amount of 1 to 10% by weight based on the total weight of the cosmetic.

The following examples further illustrate the present invention in detail but are not to be construed to limit the scope thereof. In the examples, all "parts" are by weight, unless otherwise stated.

EXAMPLE 1

An oil phase was prepared by mixing 8.0 parts of stearic acid, 2.0 parts of cetanol, 3.0 parts of glyceryl monostearate (self emulsifiable type with soap), 12.0 parts of liquid paraffin, 2.0 parts of vaseline and 0.1 parts of butyl paraben, and heating and dissolving the resulting mixture at 80° to 85° C. Separately, an aqueous phase was prepared by mixing 0.2 part of methyl paraben, 5.0 parts of propylene glycol, 1.2 parts of triethanolamine and about 6.5 parts of distilled water, heating and dissolving the resulting mixture at 75° to 80° C. The oil phase was added to the aqueous phase at 75° to 80° C. and the resulting mixture was emulsified and cooled with stirring to obtain an O/W type emulsion (pH 8.5). When the temperature of the resulting emulsion was below about 70° C., a mixture previously prepared by mixing 1.0 parts of L-ascorbic acid monostearate and 1.5 parts of liquid paraffin and kneading with a kneader was added to the emulsion, and an appropriate amount of flavor was added thereto. The latter mixture was cooled with stirring to about 30° C. to obtain a cream.

EXAMPLE 2

An oil phase was prepared by mixing 3.0 parts of stearic acid, 3.0 parts of bees wax, 3.5 parts of stearyl alcohol, 1.5 parts of polyoxyethylene sorbitan monostearate (the average molar number of added ethyleneoxide: 20), 2.0 parts of lanoline, 15.0 parts of squalane and 0.2 parts of butyl paraben, and heating and dissolving the resulting mixture at 80° to 85° C. Separately, an aqueous phase was prepared by mixing 3.5 parts of glycerin, 0.3 part of borax, 0.3 part of triethanolamine and about 60 parts of distilled water, heating and dissolving the resulting mixture at 75° to 80° C. The oil phase was added to the aqueous phase at 75° to 80° C. and the resulting mixture was emulsified and cooled with stirring to obtain an O/W type emulsion (pH 8.0). When the temperature of the emulsion was below 70° C., a mixture previously prepared by mixing 3.0 parts of L-ascorbic acid and 5.0 parts of methyl polysiloxane and kneading with a kneader was added to the emulsion. The resulting mixture was cooled with stirring to about 30° C. to obtain a cream.

EXAMPLE 3

An oil phase was prepared by mixing 3.0 parts of bees wax, 3.0 parts of cetanol, 1.0 part of polyoxyethylene sorbitan monostearate (the average molar number of added ethyleneoxide: 20), 2.5 parts of glyceryl monostearate (the self-emulsifiable type with nonionic surface active agent), 7.0 parts of isopropyl palmitate, 22.0 part of liquid paraffin and 0.2 parts of butyl paraben, and heating and dissolving the resulting mixture at 80° to 85° C. Separately, an aqueous phase was prepared by mixing 0.1 part of methyl paraben, 5.0 parts of 1,3-butyrene glycol and about 56 parts of distilled water, heating and dissolving the resulting mixture at 75° to 80° C. The oil phase was added to the aqueous phase at 75° to 80° C. and the resulting mixture was emulsified and cooled with stirring to obtain an O/W type emulsion (pH 6.0). When the temperature of the emulsion was below about 70° C., a mixture previously prepared by mixing 0.5 part of L-ascorbic acid dipalmitate and 0.5 part of a kneader was added to the emulsion. An appropriate amount of a flavor was added to the resulting mixture and cooled to about 30° C. with stirring to obtain a cream.

EXAMPLE 4

An oil phase was prepared by mixing 2.0 parts of stearic acid, 1.0 part of cetanol, 3.0 parts of vaseline, 1.0 part of lanolin alcohol, 20.0 parts of liquid paraffin and 1.5 parts of polyoxyethylene monooleate (the average molar number of added ethyleneoxide: 10) and heating and dissolving the resulting mixture at 80° to 85° C. Separately, an aqueous phase was prepared by mixing 0.2 part of methyl paraben, 5.0 parts of propylene glycol, 0.2 part of phosphoric acid and about 66 parts of distilled water, heating and dissolving the resulting mixture at 75° to 80° C. The oil phase was added to the aqueous phase at 75° to 80° C. and the resulting mixture was emulsified and cooled with stirring to obtain an O/W type emulsion (pH 5.0). When the temperature of the emulsion was below about 70° C., a mixture previously prepared by mixing 1.0 part of L-ascorbic acid dipalmitate and 3.5 parts of squalane and kneading with a kneader was added to the emulsion. An appropriate amount of flavor was added to the resulting mixture and cooled to about 30° C. with stirring to obtain a milky lotion.

EXAMPLE 5

An oil phase was prepared by mixing 8.0 parts of stearic acid, 5.0 parts of glyceryl monostearate (self-emulsifiable type with nonionic surface active agent), 5.0 parts of liquid paraffin, 1.0 part of lanolin alcohol, 1.5 parts of polyoxyethylene stearylether (the average molar number of added ethyleneoxide: 2) and heating and dissolving the resulting mixture at 80° to 85° C. Separately, an aqueous phase was prepared by mixing 0.3 part of propyl paraben, 0.07 part of carboxyvinylpolymer, 3.0 part of kaolin, 0.5 part of triethanolamine and about 74 parts of distilled water, heating and dissolving the resulting mixture at 75° to 80° C. The oil phase was added to the aqueous phase at 75° to 80° C. and the resulting mixture was emulsified and cooled with stirring to obtain an O/W type emulsion (pH 7.2). When the temperature of the emulsion was below about 70° C., a mixture previously prepared by mixing 0.5 part of L-ascorbic acid monopalmitate and 1.5 parts of liquid paraffin and kneading with a kneader was added to the emulsion. An appropriate amount of flavor was added to the resulting mixture and cooled to about 30° C. with stirring to obtain a cream mask.

What is claimed is:
1. An emulsion cosmetic containing stabilized Vitamin C which comprises:
   (A) an oil in water emulsion emulsified with a nonionic surface active agent selected from the group consisting of sorbitan fatty acid esters, glycerol fatty acid esters and polyoxyethylene alcohol ethers; and
   (B) a mixture of L-ascorbic acid or a fatty acid ester thereof and an oil selected from the group consisting of silicone oils, liquid paraffin, squalane, castor oil, olive oil and isopropyl myristate; said cosmetic being prepared by:
     (1) first admixing said oil with said L-ascorbic acid or a fatty acid ester thereof within a weight ratio of said oil to said L-ascorbic acid or a fatty acid ester thereof, being about 1:0.5 to 4; and
     (2) mixing said mixture with said oil in water emulsion in an amount of 1 to 10% by weight, based on the total weight of the resultant emulsion cosmetic.
2. An emulsion cosmetic according to claim 1, wherein said mixture is thoroughly kneaded after admixing said oil with said L-ascorbic acid or a fatty acid ester thereof and before mixing said mixture with said oil in water emulsion.
3. An emulsion cosmetic according to the claim 1, wherein the oil in water emulsion is weakly acidic.
4. An emulsion cosmetic according to claim 1, wherein the fatty acid ester is a mono-, di- or triester of a fatty acid having 10 or more carbon atoms.
5. An emulsion cosmetic according to claim 4, wherein the fatty acid ester in a member selected from the group consisting of monopalmitate, dipalmitate, monostearate and distearate of L-ascorbic acid.

* * * * *